United States Patent
Ruijters et al.

(10) Patent No.: US 11,123,025 B2
(45) Date of Patent: Sep. 21, 2021

(54) ISO-CENTERING IN C-ARM COMPUTER TOMOGRAPHY

(71) Applicant: KONINKLIJKE PHILIPS N.V., Eindhoven (NL)

(72) Inventors: Daniel Simon Anna Ruijters, Eindhoven (NL); Fred Simon Berend Van Nijnatten, Eindhoven (NL); Javier Olivan Bescos, Eindhoven (NL); Ronaldus Petrus Johannes Hermans, Heeze (NL); Adrie Baselmans, Waalre (NL); Ina Klein Teeselink, Eindhoven (NL); Jeroen Gerard Scheepens, Best (NL); Walter Everard Carels, Best (NL); Thijs Grunhagen, Eindhoven (NL)

(73) Assignee: KONINKLIJKE PHILIPS N.V., Eindhoven (NL)

(*) Notice: Subject to any disclaimer, the term of this patent is extended or adjusted under 35 U.S.C. 154(b) by 145 days.

(21) Appl. No.: 16/483,899

(22) PCT Filed: Jan. 29, 2018

(86) PCT No.: PCT/EP2018/052042
§ 371 (c)(1),
(2) Date: Aug. 6, 2019

(87) PCT Pub. No.: WO2018/145930
PCT Pub. Date: Aug. 16, 2018

(65) Prior Publication Data
US 2020/0093447 A1    Mar. 26, 2020

(30) Foreign Application Priority Data
Feb. 9, 2017 (EP) ................................ 17155385

(51) Int. Cl.
*A61B 6/08* (2006.01)
*A61B 6/03* (2006.01)
(Continued)

(52) U.S. Cl.
CPC ............ *A61B 6/08* (2013.01); *A61B 6/032* (2013.01); *A61B 6/0487* (2020.08);
(Continued)

(58) Field of Classification Search
CPC ......... A61B 6/032; A61B 6/0487; A61B 6/08; A61B 6/4085; A61B 6/4441; A61B 6/461;
(Continued)

(56) References Cited

U.S. PATENT DOCUMENTS 5,457,724 A * 10/1995 Toth .................... A61B 6/032
378/205
8,000,445 B2 * 8/2011 Mollus ................ A61B 6/488
378/98
(Continued)

FOREIGN PATENT DOCUMENTS

DE    102007005377 A1    7/2008
JP    2007202842 A        8/2007
(Continued)

OTHER PUBLICATIONS

Machine translation of JP 2012130542 (Year: 2012).*
PCT/EP2018/052042 ISR & Written Opiniion, dated Feb. 9, 2017, 12 Pages.

*Primary Examiner* — Dani Fox
*Assistant Examiner* — Soorena Kefayati

(57) ABSTRACT

An apparatus for medical imaging of a patient, including an object of interest, is provided. The apparatus comprises a patient support unit, a processor, and a display. The patient support unit is configured to receive a patient. The processor
(Continued)

is configured to receive scout images of the patient acquired in respective positions of the apparatus. Each respective position is represented by a position parameter. The processor is further configured to select at least one iso-centering image from the scout images by geometrical calculation using the position parameter of each scout image and a position parameter representing a present position of the apparatus. The processor is further configured to adapt the appearance of the at least one iso-centering image according to the present position of the apparatus. The display is configured to present the at least one adapted iso-centering image.

20 Claims, 2 Drawing Sheets

(51) Int. Cl.
 *A61B 6/00* (2006.01)
 *A61B 6/04* (2006.01)
(52) U.S. Cl.
 CPC .......... *A61B 6/4085* (2013.01); *A61B 6/4441* (2013.01); *A61B 6/461* (2013.01); *A61B 6/466* (2013.01); *A61B 6/469* (2013.01); *A61B 6/488* (2013.01); *A61B 6/5223* (2013.01); *A61B 6/545* (2013.01); *A61B 6/589* (2013.01)
(58) Field of Classification Search
 CPC ......... A61B 6/466; A61B 6/469; A61B 6/488; A61B 6/5223; A61B 6/545; A61B 6/589
 See application file for complete search history.

(56) References Cited

U.S. PATENT DOCUMENTS

| | | | | |
|---|---|---|---|---|
| 2003/0052879 | A1* | 3/2003 | Barth | G06T 11/005 345/424 |
| 2003/0165216 | A1* | 9/2003 | Walker | A61B 6/544 378/108 |
| 2005/0089139 | A1* | 4/2005 | Sukovic | A61B 6/4441 378/20 |
| 2007/0009079 | A1* | 1/2007 | Chen | A61B 6/032 378/4 |
| 2008/0198972 | A1* | 8/2008 | Rasche | A61B 6/469 378/195 |
| 2012/0155605 | A1* | 6/2012 | Yazaki | A61B 6/405 378/8 |
| 2013/0281838 | A1* | 10/2013 | Trumer | G06T 7/0012 600/424 |
| 2013/0336445 | A1* | 12/2013 | Sehnert | A61B 6/487 378/42 |
| 2013/0343511 | A1* | 12/2013 | Shukla | A61B 6/5264 378/6 |
| 2014/0185740 | A1* | 7/2014 | Chen | A61B 6/545 378/4 |
| 2015/0094567 | A1* | 4/2015 | Pfister | A61B 6/463 600/424 |
| 2015/0297166 | A1* | 10/2015 | Goto | A61B 6/469 378/15 |
| 2015/0374314 | A1* | 12/2015 | Maack | A61B 6/588 378/62 |
| 2016/0000303 | A1* | 1/2016 | Klein | A61B 6/5223 600/103 |
| 2016/0296180 | A1* | 10/2016 | Malm | A61B 6/032 |
| 2017/0018078 | A1* | 1/2017 | Liu | G06T 7/33 |
| 2017/0086758 | A1* | 3/2017 | McCarthy | A61B 6/542 |
| 2018/0049715 | A1* | 2/2018 | Zebaze | A61B 6/505 |
| 2018/0092613 | A1* | 4/2018 | Ancar | A61B 6/08 |
| 2018/0184997 | A1* | 7/2018 | Tsukagoshi | A61B 5/0033 |
| 2018/0350078 | A1* | 12/2018 | Sun | A61B 6/032 |
| 2019/0320995 | A1* | 10/2019 | Amiri | A61B 6/463 |
| 2019/0336087 | A1* | 11/2019 | Jarva | A61B 6/04 |
| 2020/0085385 | A1* | 3/2020 | Nye | A61B 6/5247 |

FOREIGN PATENT DOCUMENTS

| | | | |
|---|---|---|---|
| JP | 2012130542 | * | 7/2012 |
| JP | 2012130542 | A | 7/2012 |
| WO | 2007031945 | A2 | 3/2007 |
| WO | 2015121301 | A1 | 8/2015 |

* cited by examiner (a)

(b)

ISO-CENTERING IN C-ARM COMPUTER TOMOGRAPHY

CROSS-REFERENCE TO PRIOR APPLICATIONS

This application is the U.S. National Phase application under 35 U.S.C. § 371 of International Application No. PCT/EP2018/052042, filed on Jan. 29, 2018, which claims the benefit of European Patent Application No. 17155385.2, filed on Feb. 9, 2019. These applications are hereby incorporated by reference herein.

FIELD OF THE INVENTION

The present invention relates to iso-centering an object of interest prior to cone beam computer tomography (CBCT) scanning for examination of a patient in a C-arm examination apparatus, and relates in particular to a method for applying geometry changes to pre-acquired scout images and.

BACKGROUND OF THE INVENTION

Cone beam computer tomography (CBCT) in the context of this invention involves a C-arm of an according examination apparatus following a rotational trajectory, for example a circular trajectory or any other applicable trajectory that can be used to acquire tomographic reconstructions, around the object of interest, while acquiring images. In an example, six hundred images are acquired over a rotation angle of approximately 180 degrees. This allows to reconstruct, by a computer, a tomographic volume of the object of interest. The rotation point of this movement is known to be called the iso-center.

Before the rotational acquisition is made, the patient may be positioned on a table of the examination apparatus, such that the patient's anatomy of interest is within the field of view. This may be done by moving the patient table longitudinally and laterally (panning) and changing its height, while checking on the fluoroscopy image the relevant landmarks.

Iso-centering involves panning the table laterally and transversally, and adjusting the table height to put the relevant anatomy (the region of interest) in the iso-center position. To verify that the region of interest is indeed in the iso-center, the fluoroscopy pedal is kept pressed during the table movement, or immediately afterwards. Thereby the patient and the clinical staff are exposed to X-ray radiation.

Furthermore, to verify the position after table panning, it is desirable to look from the antero-posterior (AP) position, whereas to verify the position after table height changes, it is best to look from the lateral position. To do both on a monoplane C-arm, one needs to move the C-arm between AP and lateral positions, which takes time.

SUMMARY OF THE INVENTION

There may be a need to provide facilitated positioning and to overcome or at least minimize these drawbacks.

The object of the present invention is solved by the subject-matter of the independent claims; further embodiments are incorporated in the dependent claims.

It should be noted that the following described aspects of the invention apply also for the apparatus, the method, the computer program element and the computer readable medium.

According to a first aspect of the invention, an apparatus for medical imaging of a patient including an object of interest is provided, for example an imaging apparatus configured for CBCT scanning.

In an embodiment, the apparatus comprises a patient support unit, an acquisition unit, a data processing and control unit, and a display unit.

The patient support unit is configured to receive a patient. The data processing and control unit is configured to i) receive at least one scout image of the patient acquired in respective positions of the apparatus, the positions being represented by at least one position parameter;

ii) select at least one iso-centering image from the scout images by a geometrical calculation using at least one position parameter of the scout images and a corresponding at least one position parameter representing a present position of the apparatus, and iii) adopt the appearance of the at least one iso-centering image in accordance with the present position of the apparatus. The display unit is configured to display the adopted iso-centering image.

According to a second aspect of the invention, a method is provided for positioning an object of interest in a medical imaging apparatus, for example, for positioning the object of interest relative to an iso-center for a CBCT examination of a patient, using a C-arm imaging apparatus.

In an embodiment, the method comprises the steps of receiving at least one scout image of the patient acquired in respective positions of the examination apparatus, the positions being represented by at least one position parameter; selecting at least one iso-centering image from the scout images by a geometrical calculation using at least one position parameter of the scout images and a corresponding at least one position parameter representing a present position of the acquisition unit and/or the patient support unit; adopting the appearance of the at least one iso-centering image in accordance with the present position of the apparatus, and displaying the at least one adopted image.—

Thus, the method comprises the step of receiving a scout image. The scout images may have been previously acquired in respective positions of the apparatus. The position of the apparatus at the time of acquiring a scout image may be represented by one or more position parameters.

The method further comprises the step of selecting at least one iso-centering image from the scout at least one of the position parameters of the scout images and a corresponding position parameter representing a present position of the apparatus, for example, positions of units of the apparatus such as a C-arm and the patient support unit.

The selection may involve a geometrical calculation involving the at least one position parameter, for example, determining a distance between position parameter sets for the scout image and the present position of the apparatus, as described hereinafter in more detail.

The method further comprises the step of adopting the appearance of the at least one iso-centering image in accordance with the present position of the apparatus. The thus adopted iso-centering image may provide guidance for adjusting the apparatus from the present position to an iso-center position with respect to the object of interest.

For example, an appearance of the iso-centering image may be adopted in correspondence with the present position or orientation of the C-arm; for example, the adaptation is such that the appearance of the iso-centering image is as if taken at the present C-arm orientation.

In an alternative, irrespective of the present C-arm orientation, an iso-centering image in an anterior-posterior (AP)

or lateral perspective is adopted in accordance with the present position of the C-arm and/or the patient support. In this respect, an AP view is a "top-down" view of the patient on the patient support, while a lateral view is a side view or "left-to-right" view of the patient. The AP view and the lateral view are approximately perpendicular to each other.

In a further example, the iso-centering image is adapted by indicating the iso-center according to the present position (the "present iso-center") in the iso-centering image. In other words, the iso-center of a CBCT examination, i.e. a rotational image acquisition, if it were carried out using the present positions of the C-arm and patient support, can be indicated in the iso-centering image.

The method may further comprise a step of displaying the at least one adopted iso-centering image, for example on a display device.

Thus, if a user observes in the displayed iso-centering image that the iso-center is not accurately positioned within the object of interest, he may adjust the position of the C-arm and/or patient support so as to better align the iso-center with the object of interest. Thus, a representation of the present iso-center may be shown to a user as visual guidance for accurate iso-centering the apparatus for an upcoming CBCT examination.

According to an example, the step of selecting an iso-centering image from the scout images includes selecting a scout image acquired in an AP or lateral direction and thus having an AP or lateral perspective.

Alternatively, in the selecting step a scout image acquired in a different direction is selected and the adopting step includes a transformation of the iso-centering image is transformed so that it appears in an AP or lateral perspective.

According to an example, the step of displaying the at least one adopted image on a display device includes displaying at least two iso-centering images next to each other on the display device including one having an AP perspective and one having a lateral perspective. For example, each image is displayed together with a visual guidance for iso-centering, such as a representation of the present iso-center.

According to a further example, the adopted iso-centering image may further comprise a range of the CBCT scan relative to the image, in other words, an indication of a volume that would be acquired if a CBCT examination were carried out using the present positions of the C-arm and patient support.

According to a further example, the step of selecting an iso-centering image from the stored images is performed by determining the iso-centering image as being the one which comprises the object of interest most centrally and/or the position parameters of which are locally closest and/or least biased perspectively or least distorted relative to the parameters of the current position of the apparatus.

According to a further example, the scout images have been acquired by an X-ray acquisition unit, however alternatively or in addition, for example an ultrasound or optical acquisition unit may be used. A scout image may also be a projection from a 3D image, such as a CT or MR image.

In a further example, the scout images have been acquired by the acquisition unit itself, for example during an examination of the same patient carried out prior to the CBCT examination, for which iso-centering is to be done. Also scout images from earlier examinations may be used.

According to a further exemplary embodiment, in order to apply any movements of the patient support or table and/or of the C-arm onto the adopted iso-centering image, the method comprises repeating the step of adopting the appearance of the iso-centering image based on the updated positions. If necessary, also the selecting step may be repeated to select a more appropriate scout image as the new iso-centering image, for example if another scout image is closer to the updated position of the apparatus than the original scout image.

In this case, for example, the geometrical calculation may be repeated now using at least one position parameter of the updated position of the apparatus.

According to a further exemplary embodiment, geometrical calculation is performed using at least one position parameter (for example, a point of origin within a coordinate system, size, scale, direction of view, vanishing point and/or perspective orientation) of the iso-centering image, the image parameter resulting from the respective position (of the apparatus during acquisition of the iso-centering image and/or at least one image parameter of a CBCT scan, if taken in the present position of the apparatus.

As scout images, fluoroscope and exposure acquisitions of a preceding exam of the present patient can be obtained, along with their geometry information (C-arm viewing incidence, L-arm position, detector position, table height, etc.). During the iso-centering, for example AP and lateral images that are closest to the current table position can be displayed as the iso-centering images. Furthermore, a graphic overlay can indicate the region of interest that will be reconstructed if a CBCT examination were to be carried out at the current position of the apparatus.

If necessary, the adoption of the iso-centering image may include a translation and/or zooming operation so as to match the image with a current table position and/or a current position of the acquisition unit. In an example, if this operation results in an adopted image having only partial coverage for a field of view of the apparatus in its current position, this is suitably indicated for example by adding one or more areas of solid color to the image.

For example, when a clinical user "pans" the table i.e. moves it horizontally and/or laterally with the table top and patient remaining in the same plane, the displayed images preferably pan along to reflect their content with respect to the current table position. The same applies for table height changes.

When the table is moved to a position where a better matching scout image is available, the latter may be selected as a new iso-centering image and displayed.

Because of the perspective at image acquisition, it may be difficult to correct the complete visible scene in a scout image to adjust it to the current patient support position. Therefore, preferably, any transformation of the iso-centering image focuses on the present iso-center position as a point of reference.

Anatomical structures, for example in or around the object of interest, can be magnified differently due to the perspective and distance relative to the acquisition unit, for example the X-ray source and detector. A magnification factor at a "fixed point" above the table, for example a certain height (e.g. 15 cm) above the table, can be used as a compromise. In an example, it may be calculated as follows: m=SID/SOD, whereby m stands for magnification factor, SID for source-to-image distance (also called source-to-detector distance), and SOD for source-to-object distance (the distance of the X-ray source to the fixed point over the table). The SOD can be varied by changing the table height, while the SID can be varied by moving the detector.

Panning the table, i.e. moving the table parallel to the top of the patient support, translates (pans) the iso-centering image along with table movement, or alternatively moves a graphical representation in the iso-centering image indicating the reconstruction field of view by the same distance in the opposite direction.

When a table or support of a C-arm CT apparatus is moved along a vector aligned different than parallel with respect to the table top, i.e. when the movement also include a displacement along the z-axis (table height), the movement vector can be decomposed, according to an example, into a parallel translational vector, and a change of the SOD perpendicular to the plane.

During acquiring scout images, prior to the iso-centering, all images are stored along with their geometry information (e.g., C-arm viewing incidence, L-arm position, detector position, table height, etc.) and time of creation.

For example: the geometry information may be represented by a parameter set denoted as P, which consists of a set of parameters $(p_1, \ldots, p_N)$, wherein $p_n$ stands for a particular parameter (e.g., SID, or table height, or creation time).

Generally, a distance between two parameter sets can then be defined as $d(P_1, P_2)$ and indicates the similarity between the two sets. The geometric calculation may then include determining such distance, which can for example be calculated as $$d(P_1, P_2) = \sum_{n=1}^{N} w_n \cdot (p_{n,1} - p_{n,2}),$$

wherein $w_n$ indicates the contribution of each parameter difference as a weighting factor. Other distance functions are also possible (e.g., setting the distance to infinite when a certain parameter $p_{n,1}-p_{n,2}$ is larger than a predefined threshold).

Preferably, for each image that is acquired, the parameter set P, which reflects the geometry at the time of acquisition, is stored.

During iso-centering, it is preferred that at least one of an AP image and a lateral image are shown simultaneously, for example in a side by side view. The AP and lateral image can be selected as follows: for each image, a parameter set $P_{view}$ is assembled representing the geometry information for the present C-arm position. For example, the C-arm view parameters (rotation and angulation) can be set to a predefined value, for example 0,0 for AP, and the other parameters can be filled in based on the current geometry position (table position, L-arm translation, etc.).

The parameter sets of the available scout images are then compared to this $P_{view}$, evaluating the earlier defined distance $d(P_{image}, P_{view})$, and a scout image is selected based on the outcome of the evaluation. For example, a scout image for which the parameter set has the smallest distance to the parameter set of an AP view and/or a lateral view in the present position is selected for display.

In other words, in an example, a plurality of scout images may be available, and the distance calculation is carried out for at least a part of the scout images. One of the scout images is then selected as the iso-centering image based on the calculation results; in particular, as the iso-centering image, the scout image with the smallest parameter set distance to a "virtual" AP or lateral view in the present position of the imaging apparatus is selected.

As said, AP and lateral views preferably are presented simultaneously e.g. side by side, or above each other, or on two separate monitors. Optionally, in the same view an estimated typical reconstruction cube or cone, in particular showing the range or field of view of a C-arm CT examination, can be shown.

During geometry changes (e.g. panning) of the patient support, the iso-centering images preferably are updated (panned or zoomed or replaced by an image with a smaller parameter distance) in real-time. Since visual guidance can be given to a user, like a physician using the apparatus or method according to one of the examples, regarding the effect of the current geometry position with respect to the iso-centering image and thereby the position of an iso-center if a CBCT examination were carried out at the current position, there is no need to create a new X-ray image for assessing the iso-centering nor, in an example, for assessing the field of view.

Small patient movements might be neglected, since iso-centering is typically not invalidated by a few millimeters offset. Large patient motions (e.g., repositioning the patient by clinical staff), however, can "invalidate" the scout images, as, in particular, the geometrical situation has changed and thus the stored position parameters do not reflect any more the present orientation of the object of interest depicted in the images. Therefore, in an embodiment, automatic patient tracking, for example using depth cameras or sensors connected to the patient, can be used to establish large patient movements. In an example, at least one position parameter of the scout images may then be corrected by an offset representing the established patient movement.

In an example of adopting the iso-centering image, the iso-centering image is moved and/or zoomed with respect to a fixed reconstruction cube or square as an indication of the CBCT range. Alternatively or in addition, it is possible to move and/or zoom such reconstruction cube within the iso-centering image in an opposite manner.

In an example of selecting scout images, instead of selecting iso-centering images representing an AP and lateral view, any number of views from any predefined viewing angle can be selected. For example, an iso-centering images may correspond to the current C-arm orientation. Alternatively, specific view orientations may be defined by the user and corresponding scout images may be selected as an iso-centering image accordingly.

In a further example of selecting a scout image, a threshold may be applied to the distance $d(P_{image}, P_{view})$, meaning that when the smallest found distance is larger than this threshold, no iso-centering image is selected and shown for a particular view. When no image is shown for a view, a warning indicator may be provided instead. In addition or alternatively, instruction regarding how to acquired this view may be shown.

In a further example, instead of adopting one or more previously acquired scout images and visualize the current isocenter and/or field of view, it is also possible to let a user indicate the desired isocenter and/or field of view on the iso-centering images by user interaction, e.g. by clicking on an image, and to move the patient support (table) and/or acquisition unit (C-arm) to the desired position automatically, using a motorized positioning system.

In a further example, in order to reduce dose to sensitive organs, for example the eyes in a head scan, it may also be possible to change the axis of rotation of a C-arm with respect to the orientation of the patient, in addition to positioning the patient in x-, y-, and z-direction. Changing the axis of rotation of the C-arm could for example result in a CBCT examination using an angulated roll scan with the C-arm in a side-position. Changing the orientation of the patient could for example be achieved by tilting the patient support (table) laterally, i.e. sideways.

The particular positioning in accordance with embodiments of the apparatus and method can also be referred to as "zero radiation" iso-centering, since iso-centering can be achieved using existing scout images, and no separate X-ray acquisitions are required for the specific purpose of iso-centering itself.

As an alternative or in addition to previously acquired X-ray scout images, also images of different sources can be used. For example, if the region of interest is already visualized by e.g. ultra sound, and the ultra sound is registered geometrically with respect to the C-arm CT apparatus, then these ultra sound images can be used as well. Alternatively, optical images can be used, e.g., acquired by cameras attached to the C-arm gantry. Alternatively, virtual projection images may be generated from a 3D scout image acquired using, for example, a CT or MR imaging system.

Instead of using the embodiments of the method for purpose of iso-centering in preparation for a CBCT examination, these embodiments may also be advantageously applied in other X-ray acquisitions in which adjusting a 3D position of the acquisition unit and/or patient support unit with respect to a region of interest is relevant.

In an example, visual guidance may be provided to restore the position of a mobile imaging system, for example a C-arm on a cart used in orthopaedic or vascular treatments, to a position and optionally an orientation in which an earlier examination, or an earlier phase of such exemplary treatment, was carried out. In this example, scout images from the earlier examination are adopted to a current position and optionally orientation of the mobile C-arm, and a graphical representation in a positioning image i.e. the selected scout image may, for example, comprise an indication of a field of view of the mobile C-arm for its current position and orientation These and other aspects of the present invention will become apparent from and be elucidated with reference to the embodiments described hereinafter.

BRIEF DESCRIPTION OF THE DRAWINGS

Exemplary embodiments of the invention will be described in the following with reference to the following drawings.

DETAILED DESCRIPTION OF EMBODIMENTS

In the following, the invention is exemplarily described as being used in the context of a C-arm CT examination apparatus 10.

Figure 1:
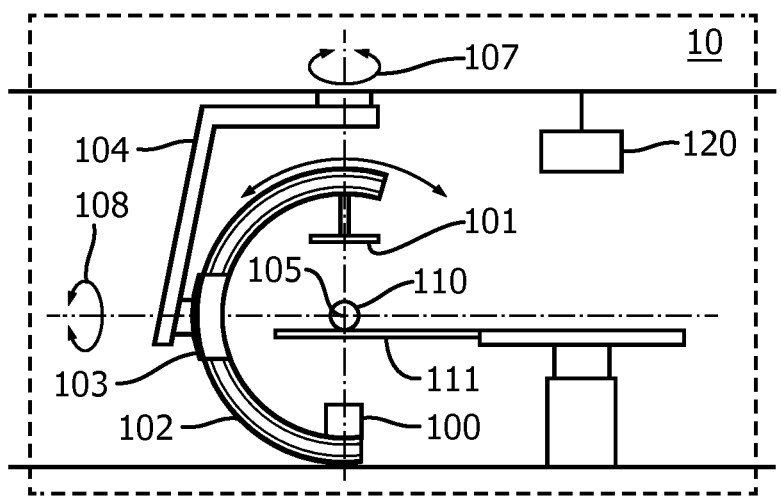
FIG. 1 is a schematic side view of an example of a C-arm examination apparatus.
Figure 2:
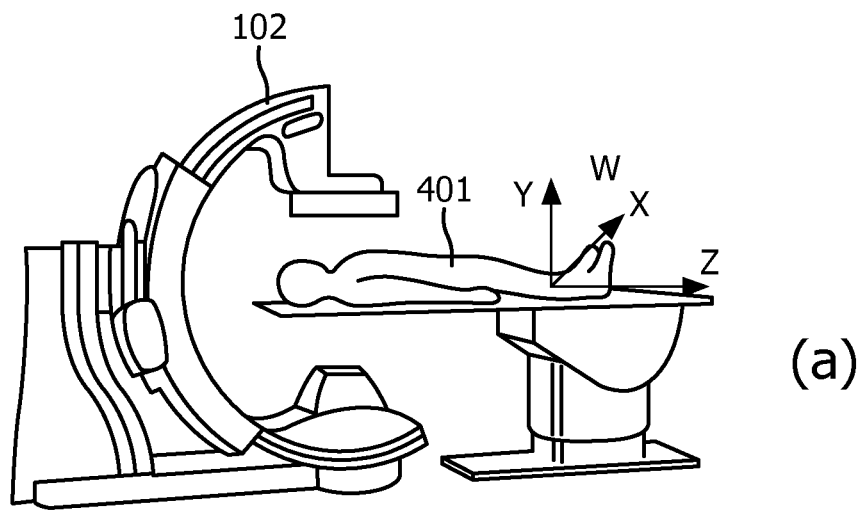
FIG. 2a, 2b are schematic views of an example of a C-arm examination apparatus in AP and lateral view position of the C-arm during examination of a patient.
Figure 2:
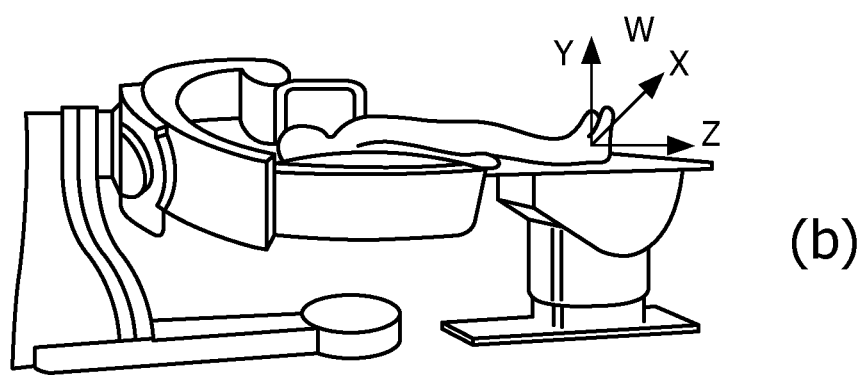
Figure 3:
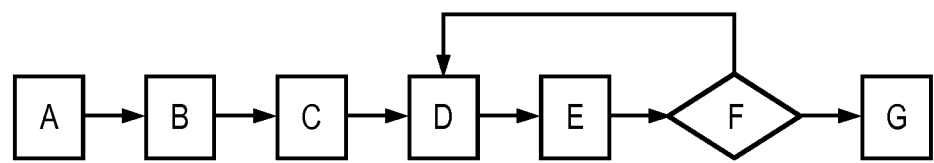
FIG. 3 is a flow diagram of an example of a method.

FIGS. 1 and 2 schematically show a C-arm examination apparatus 10 adapted for CBCT scanning for examination of a patient 401, by which the method according to FIG. 3 may be carried out.

According to FIG. 3, a flow diagram represents the following steps of a method for positioning an object of interest 110, and in particular iso-centering of the object.

Iso-centering means adjusting geometrical, spatial parameters relative to each other of the units of the apparatus 10, namely the L-arm 104, C-arm 102, X-ray source 100, X-ray detector 101 and patient support 111, such that position of the iso-center 105 of the apparatus 10—i.e. intersection 105 of the horizontal rotation axis (depicted in chain-line) of the C-arm 102 and of the view axis (direction of view of the CT scanning and image acquisition unit 100, 101; depicted in chain-line, vertical in the depicted state of the apparatus 10) is positioned within the object of interest 100, e.g., the head 110 of the patient 401) prior to cone-beam computer tomography (CBCT) scanning for examination of a patient 401 in a C-arm examination apparatus 10.

As indicated in FIG. 1, in an example, the C-arm CT examination apparatus 10 comprises a patient support 111, an acquisition unit including a C-arm 102, a data processing and control unit (not shown) and a display unit 120.

In an example, the method comprises:

A) receiving scout images of the patient 401 including the object of interest 110 previously acquired by an X-ray acquisition unit in the C-arm examination apparatus 10 in respective positions of the apparatus represented by at least one position parameter.

The scout images may be images that had been acquired previous to the procedure or examination in which iso-centering or, more generally, positioning of the apparatus with respect to an object of interest, is to be performed. For example, pre-procedural diagnostic images or navigation images stored in an image buffer, or a database such as a PACS system, can be re-used as scout images for purpose of iso-centering.

The at least one position parameter for example includes a viewing direction of the acquisition unit represented by a rotation (angle of roll motion 107) and/or angulation (angle of propeller motion 108) of the C-arm 102, a three-dimensional position of an L-arm 104 supporting the C-arm, a three-dimensional position of the patient support 111 and a height of the detector 101 above the object of interest 110 and/or a source-imager distance (SID) and/or a source-object distance (SOD).

A a present position of the apparatus can be represented by similar position parameters. Optionally, the method comprises B) adjusting the position of the apparatus 10 roughly into the present position of be used for CBCT scanning of the object of interest 110. For example, a physician may manually move the apparatus to an approximate position for a CBCT examination to be carried out. In an alternative example, a physician may manually select an available scout image, and the apparatus moves automatically to the corresponding position.

The method further comprises

C) selecting, from the scout images, at least one iso-centering image by a geometrical calculation using at least one of the position parameters of the scout images and a corresponding position parameter representing a present position of the apparatus.

For example, one iso-centering image acquired in AP direction, as it is shown in FIG. 2a, and one iso-centering image acquired in lateral direction, as it is shown in FIG. 2b, are selected from the available scout images. In particular, the respective iso-centering images are determined as being the ones, which comprises the object of interest 110 most centrally and complete and respectively.

The selection is based on a geometrical calculation, for example a determination of a minimum in a distance function between the position parameter sets of each scout image relative to the position parameter set representing the present position of the apparatus.

The method further comprises

D) adopting the appearance of the at least one iso-centering image, such that the appearance of the iso-centering images in accordance with the present position of the apparatus, for example with the positions of the C-arm 102 and the patient support 111.

Figure 4:
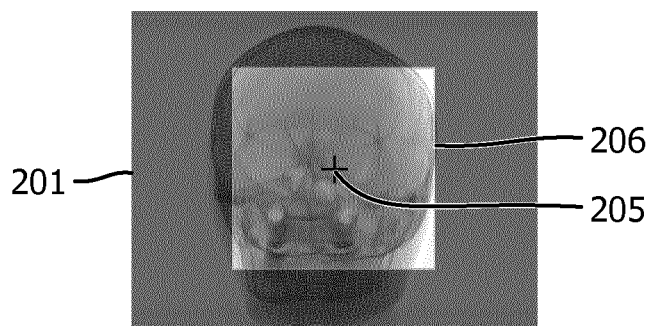
FIG. 4 is an example of a display of a display unit during examination of a patient.
Figure 4:
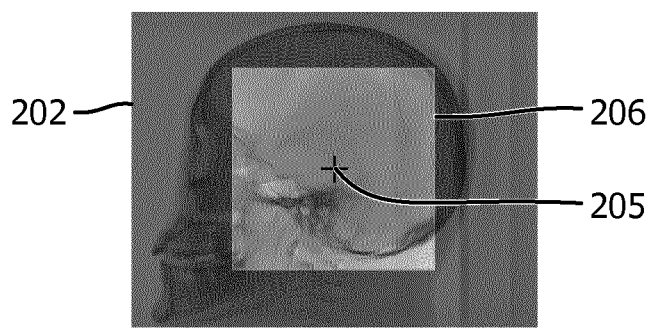

FIG. 4 shows an example of two adopted iso-centering images, one AP view 201 and one lateral view 202. The adopted images further include a representation 205 of the iso-center 105 of the apparatus according to its current position, as well as a boundary box 206 representing a reconstruction cube i.e. a volume that would be reconstructed if a CBCT examination were carried out using the apparatus in its current position. In other words, the boundary boxes indicate a present range of a CBCT scan to be carried out at the present position.

The method further comprises

E) displaying the two adopted iso-centering images next to each other on a display device.

In an option it is provided;

F) determining a change in a position of the apparatus, for example of the C-arm 102 or patient support 111, i.e. whether the user adjusted the position of any unit of the apparatus leading to a change in the present position parameters.

If so, and the movement optionally exceeds a threshold, the steps of selecting and adopting the iso-centering images can be repeated. It may be that the previously selected respective iso-centering image is still the one, which comprises the object of interest 110 most centrally and complete; alternatively, it may be that a different scout image is selected as a new iso-centering image as it is closer to the updated position of the apparatus.

In either case, the iso-centering image is adapted to the updated position of the apparatus, which may involve a new transformation of the image and/or updating the representations 205 of the iso-centering position and the boundary box 206 representing the CBCT scan range.

If there is no movement, and the user optionally confirms that the systems has been brought to the desired position for the examination to be performed, the method proceeds to be optional step of performing the examination, in particular:

G) CBCT scanning the region of interest 110.

It is understood that, without repeating here all the examples and explanations provided with reference to the method of the invention, the apparatus of the invention is intended as being arranged to carry out the above described method steps. Thus, all of the above examples and explanations, although provided with reference to the method, are also to be intended as being implemented by the apparatus. This can be achieved, for example, by suitable hardware and/or software.

In another exemplary embodiment of the present invention, a computer program or a computer program element is provided that is characterized by being adapted to execute the method steps of the method according to one of the preceding embodiments, on an appropriate system. In other words, in the preceding examples, the method may be a computer-implemented method.

The computer program element might be stored on a computer unit, which might also be part of an embodiment of the present invention. This computing unit may be adapted to perform or induce a performing of the steps of the method described above. Moreover, it may be adapted to operate the components of the above described apparatus. The computing unit can be adapted to operate automatically and/or to execute the orders of a user. A computer program may be loaded into a working memory of a data processor. The data processor may thus be equipped to carry out the method of the invention.

This exemplary embodiment of the invention covers both, a computer program that right from the beginning uses the invention and a computer program that by an up-date turns an existing program into a program that uses the invention.

Further on, the computer program element might be able to provide all necessary steps to fulfil the procedure of an exemplary embodiment of the method as described above.

According to a further exemplary embodiment of the present invention, a computer readable medium, such as a CD-ROM, is presented wherein the computer readable medium has a computer program element stored on it which computer program element is described by the preceding section. A computer program may be stored and/or distributed on a suitable medium, such as an optical storage medium or a solid-state medium supplied together with or as part of other hardware, but may also be distributed in other forms, such as via the internet or other wired or wireless telecommunication systems. However, the computer program may also be presented over a network like the World Wide Web and can be downloaded into the working memory of a data processor from such a network. According to a further exemplary embodiment of the present invention, a medium for making a computer program element available for downloading is provided, which computer program element is arranged to perform a method according to one of the previously described embodiments of the invention.

It has to be noted that embodiments of the invention are described with reference to different subject matters. In particular, some embodiments are described with reference to method type claims whereas other embodiments are described with reference to the device type claims. However, a person skilled in the art will gather from the above and the following description that, unless otherwise notified, in addition to any combination of features belonging to one type of subject matter also any combination between features relating to different subject matters is considered to be disclosed with this application. However, all features can be combined providing synergetic effects that are more than the simple summation of the features.

While the invention has been illustrated and described in detail in the drawings and foregoing description, such illustration and description are to be considered illustrative or exemplary and not restrictive. The invention is not limited to the disclosed embodiments. Other variations to the disclosed embodiments can be understood and effected by those skilled in the art in practicing a claimed invention, from a study of the drawings, the disclosure, and the dependent claims.

In the claims, the word "comprising" does not exclude other elements or steps, and the indefinite article "a" or "an" does not exclude a plurality. A single processor or other unit may fulfil the functions of several items re-cited in the claims. The mere fact that certain measures are re-cited in mutually different dependent claims does not indicate that a combination of these measures cannot be used to advantage. Any reference signs in the claims should not be construed as limiting the scope.

The invention claimed is:

1. An apparatus for medical imaging of a patient including an object of interest, the apparatus comprising:

a patient support unit configured to receive a patient;

a processor configured to:
  i) receive at least one scout image of the patient acquired in a respective position of the apparatus, the respective position being represented by at least one position parameter,
  ii) select at least one iso-centering image from the at least one scout image by geometrical calculation using the at least one position parameter of the at least one scout image and at least one position parameter representing a present position of the apparatus, and
  iii) adapt an appearance of the at least one iso-centering image according to the present position of the apparatus; and
  a display configured to display the at least one adapted iso-centering image.

2. The apparatus according to claim 1, wherein the at least one adapted iso-centering image includes representation of a present iso-center for iso-centering.

3. The apparatus according to claim 1, wherein the processor is further configured to select as the at least one iso-centering image a scout image acquired in an AP direction and a scout image acquired in a lateral direction.

4. The apparatus according to claim 1, wherein the processor is further configured to select the at least one iso-centering image by determining a scout image of the at least one scout image having the object of interest most centrally located and/or the at least one position parameter locally closest and/or least biased perspectively relative to parameters of an adjusted position of the medical imaging apparatus.

5. The apparatus according to claim 1, wherein the processor is further configured to adapt the at least one iso-centering image by transforming the selected at least one scout image according to the present position of the medical imaging apparatus, and wherein the transforming includes a translation and/or zooming operation so as to match the at least one scout image with the present position of the medical imaging apparatus.

6. The apparatus according to claim 1, wherein the geometrical calculation is a calculation of a distance between position parameter sets of the at least one scout image and the present position.

7. A method for positioning an object of interest in a medical imaging apparatus, comprising:
  receiving at least one scout image of a patient acquired in respective position of the medical imaging apparatus, the respective position being represented by at least one position parameter;
  selecting at least one iso-centering image from the at least one scout image by geometrical calculation using the at least one position parameter of the at least one scout image and a corresponding at least one position parameter representing a present position of the medical imaging apparatus;
  adapting an appearance of the at least one iso-centering image according to the present position of the medical imaging apparatus; and
  displaying the at least one adapted iso-centering image.

8. The method according to claim 7, wherein the at least one adapted iso-centering image includes representation of a present iso-center for iso-centering.

9. The method according to claim 7, wherein selecting the at least one iso-centering image from the at least one scout image comprises selecting a scout image acquired in an AP direction and selecting a scout image acquired in a lateral direction.

10. The method according to claim 7, wherein the at least one adapted iso-centering image further includes a representation of a range of a CBCT scan relative to the at least one adapted image.

11. The method according to claim 7, wherein selecting the at least one iso-centering image includes determining the at least one iso-centering image as being the at least one scout image, which comprises the object of interest most centrally located and/or the at least one position parameter locally closest and/or least biased perspectively relative to parameters of an adjusted position of the medical imaging apparatus.

12. The method according to claim 7, wherein adapting the at least one iso-centering image includes transforming the selected at least one scout image according to the present position of the medical imaging apparatus.

13. The method according to claim 7, wherein the selecting includes a geometrical calculation of a distance between position parameter sets of the at least one scout image and the present position.

14. The method according to claim 7, further comprising:
  repeating selecting of the at least one iso-centering image and then adapting the appearance of the at least one iso-centering image including repeating the geometrical calculation using at least one position parameter of an updated position of the medical imaging apparatus.

15. The method according to claim 8, wherein the displaying comprises displaying the selected at least one iso-centering image next to each other on a display device including the representation of the present iso-center in each image.

16. The method according to claim 12, wherein the transforming includes a translation and/or zooming operation so as to match the at least one scout image with the present position of the medical imaging apparatus.

17. The method according to claim 13, wherein a scout image of the at least one scout image with a smallest parameter set distance to the present position is selected as the at least one iso-centering image.

18. A non-transitory computer-readable storage medium having stored a computer program for medical imaging of a patient including an object of interest, the computer program comprising instructions which, when executed by a processor, cause the processor to:
  i) receive at least one scout image of the patient acquired in a respective position of a medical imaging apparatus, the respective position being represented by at least one position parameter,
  ii) select at least one iso-centering image from the at least one scout image by geometrical calculation using the at least one position parameter of the at least one scout image and at least one position parameter representing a present position of the medical imaging medical imaging apparatus,
  iii) adapt an appearance of the at least one iso-centering image according to the present position of the medical imaging apparatus, and
  cause display of the at least one adapted iso-centering image.

19. The apparatus—according to claim 2, wherein the processor is further configured to display the at least one iso-centering image, including the representation of the present iso-center, next to each other on a display device.

20. The apparatus according to claim 6, wherein the processor is further configured to select a scout image of the at least one scout image with a smallest parameter set distance to the present position as the at least one iso-centering image.

* * * * *